(12) United States Patent
Ymén et al.

(10) Patent No.: US 10,183,920 B2
(45) Date of Patent: Jan. 22, 2019

(54) CRYSTAL MODIFICATIONS OF ELOBIXIBAT

(71) Applicant: Elobix AB, Göteborg (SE)

(72) Inventors: Ingvar Ymén, Saltsjö-Boo (SE);
Martin Bohlin, Johanneshov (SE);
Thomas Larsson, Bjarred (SE); Helena Nicklasson, Bjärred (SE)

(73) Assignee: Elobix AB, Göteborg (SE)

( * ) Notice: Subject to any disclaimer, the term of this patent is extended or adjusted under 35 U.S.C. 154(b) by 0 days.

(21) Appl. No.: 15/519,808

(22) PCT Filed: Oct. 23, 2015

(86) PCT No.: PCT/EP2015/074573
§ 371 (c)(1),
(2) Date: Apr. 17, 2017

(87) PCT Pub. No.: WO2016/062848
PCT Pub. Date: Apr. 28, 2016

(65) Prior Publication Data
US 2017/0240516 A1    Aug. 24, 2017

(30) Foreign Application Priority Data
Oct. 24, 2014   (EP) .................... 14190290

(51) Int. Cl.
*C07D 281/10* (2006.01)
(52) U.S. Cl.
CPC ........ *C07D 281/10* (2013.01); *C07B 2200/13* (2013.01)
(58) Field of Classification Search
CPC .................................................. C07D 281/10
See application file for complete search history.

(56) References Cited

U.S. PATENT DOCUMENTS

| | | | |
|---|---|---|---|
| 3,539,380 A | 11/1970 | Johnson | |
| 4,172,120 A | 10/1979 | Todd et al. | |
| 4,507,235 A | 3/1985 | Wunsch | |
| 5,422,124 A | 6/1995 | Valducci | |
| 5,681,584 A | 10/1997 | Savastano | |
| 5,811,388 A | 9/1998 | Friend et al. | |
| 5,994,391 A | 11/1999 | Lee et al. | |
| 6,069,167 A | 5/2000 | Sokol | |
| 6,277,831 B1 | 8/2001 | Frick et al. | |
| 6,346,527 B1 | 2/2002 | Takanaka et al. | |
| 6,355,672 B1 | 3/2002 | Yasuma et al. | |
| 6,387,924 B2 | 5/2002 | Lee et al. | |
| 6,387,944 B1 | 5/2002 | Frick et al. | |
| 6,635,280 B2 | 10/2003 | Shell et al. | |
| 6,676,979 B2 | 1/2004 | Marlett et al. | |
| 6,906,058 B2 | 6/2005 | Starke et al. | |
| 6,943,189 B2 | 9/2005 | Keller et al. | |
| 7,019,023 B2 | 3/2006 | Frick et al. | |
| 7,125,864 B2 | 10/2006 | Starke et al. | |
| 7,132,416 B2 | 11/2006 | Starke et al. | |
| 7,132,557 B2 | 11/2006 | Wilkes et al. | |
| 7,192,945 B2 | 3/2007 | Starke et al. | |
| 7,192,946 B2 | 3/2007 | Starke et al. | |
| 7,192,947 B2 | 3/2007 | Starke et al. | |
| 7,226,943 B2 | 6/2007 | Starke et al. | |
| 7,238,684 B2 | 7/2007 | Starke et al. | |
| 7,514,421 B2 | 4/2009 | Abrahamsson et al. | |
| 8,067,584 B2 | 11/2011 | Starke et al. | |
| 9,023,368 B2 | 5/2015 | Basit et al. | |
| 9,409,875 B2 | 8/2016 | Bohlin et al. | |
| 9,684,018 B2 | 6/2017 | Horanzy | |
| 9,694,018 B1 | 7/2017 | Gillberg et al. | |
| 9,701,649 B2 | 7/2017 | Bohlin et al. | |
| 9,745,276 B2 | 8/2017 | Bohlin et al. | |
| 2002/0142054 A1 | 10/2002 | Marlett et al. | |
| 2003/0124088 A1 | 7/2003 | Masuda et al. | |
| 2003/0125316 A1 | 7/2003 | Keller et al. | |
| 2003/0143183 A1 | 7/2003 | Knudsen et al. | |
| 2003/0215843 A1 | 11/2003 | Poupon et al. | |
| 2004/0067933 A1 | 4/2004 | Starke et al. | |
| 2005/0009805 A1 | 1/2005 | Sasahara et al. | |
| 2005/0113362 A1 | 5/2005 | Lindstedt et al. | |
| 2005/0124557 A1 | 6/2005 | Lindqvist | |
| 2005/0171204 A1 | 8/2005 | Lindstedt et al. | |
| 2005/0197376 A1 | 9/2005 | Kayakiri et al. | |
| 2005/0266080 A1 | 12/2005 | Desai et al. | |
| 2005/0282822 A1 | 12/2005 | Alstermark et al. | |
| 2006/0083790 A1 | 4/2006 | Anderberg et al. | |
| 2006/0210633 A1 | 9/2006 | Dharmadhikari | |
| 2007/0197522 A1 | 8/2007 | Edwards et al. | |
| 2008/0300171 A1 | 12/2008 | Balkan et al. | |
| 2009/0098200 A1 | 4/2009 | Temtsin Krayz et al. | |
| 2009/0131395 A1 | 5/2009 | Antonelli et al. | |
| 2010/0130472 A1 | 5/2010 | Young et al. | |

(Continued)

FOREIGN PATENT DOCUMENTS

| CA | 2065151 | 3/1991 |
|---|---|---|
| DE | 3930168 | 3/1991 |

(Continued)

OTHER PUBLICATIONS

U.S. Appl. No. 13/881,435, filed May 22, 2013, Gillberg et al.
U.S. Appl. No. 14/505,811, filed Oct. 3, 2014, Gillberg et al.
U.S. Appl. No. 15/230,124, filed Aug. 5, 2016, Gillberg et al.
U.S. Appl. No. 13/881,447, filed May 17, 2013, Gillberg et al.
U.S. Appl. No. 14/505,782, filed Oct. 3, 2014, Gillberg et al.
U.S. Appl. No. 15/069,355, filed Mar. 14, 2016, Gillberg et al.
U.S. Appl. No. 15/069,199, filed Mar. 14, 2016, Gillberg et al.
U.S. Appl. No. 15/276,446, filed Sep. 26, 2016, Gillberg et al.
U.S. Appl. No. 15/726,071, filed Oct. 5, 2017, Gillberg et al.
U.S. Appl. No. 15/722,110, filed Oct. 2, 2017, Gillberg et al.
U.S. Appl. No. 15/726,203, filed Oct. 5, 2017, Gillberg et al.
U.S. Appl. No. 15/894,472, filed Feb. 12, 2018, Gillberg et al.

(Continued)

*Primary Examiner* — Bruck Kifle
(74) *Attorney, Agent, or Firm* — Fish & Richardson P.C.

(57) ABSTRACT

The present invention relates to crystal modifications of N-{(2R)-2-[({[3,3-dibutyl-7-(methylthio)-1,1-dioxido-5-phenyl-2,3,4,5-tetrahydro-1,5-benzothiazepin-8-yl]oxy}acetyl)amino]-2-phenylethanolyl}glycine (elobixibat).

24 Claims, 8 Drawing Sheets

(56) References Cited

U.S. PATENT DOCUMENTS

| | | |
|---|---|---|
| 2010/0286122 A1 | 11/2010 | Belyk |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |

FOREIGN PATENT DOCUMENTS

| | | |
|---|---|---|
| DE | 19825804 | 8/2000 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1273307 | 1/2003 |
| EP | 1535913 | 6/2005 |
| EP | 1719768 | 11/2006 |
| GB | 2262888 | 7/1996 |
| JP | A-2004-516285 | 6/2004 |
| JP | B-3665055 | 6/2005 |
| JP | 2006/124695 | 5/2006 |
| JP | B-4870552 | 2/2012 |
| JP | A-2013-542953 | 11/2013 |
| JP | B-5421326 | 2/2014 |
| WO | WO 93/16055 | 8/1993 |
| WO | WO 94/00111 | 1/1994 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | WO 98/03818 | 1/1998 |
| WO | WO 98/07449 | 1/1998 |
| WO | WO 98/38182 | 9/1998 |
| WO | WO 98/40375 | 9/1998 |
| WO | WO 99/01149 | 1/1999 |
| WO | WO 99/32478 | 1/1999 |
| WO | WO 99/35135 | 7/1999 |
| WO | WO 99/64409 | 7/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 01/60807 | 8/2001 |
| WO | WO 01/66533 | 9/2001 |
| WO | WO 01/68096 | 9/2001 |
| WO | WO 01/68637 | 9/2001 |
| WO | WO 02/08211 | 1/2002 |
| WO | WO 02/09815 | 4/2002 |
| WO | WO 02/32428 | 4/2002 |
| WO | WO 02/50051 | 6/2002 |
| WO | WO 02/53548 | 6/2002 |
| WO | WO 03/020710 | 3/2003 |
| WO | WO 03/022286 | 3/2003 |
| WO | WO 03/022804 | 3/2003 |
| WO | WO 03/022825 | 3/2003 |
| WO | WO 03/022830 | 3/2003 |
| WO | WO 03/051821 | 6/2003 |
| WO | WO 03/051822 | 6/2003 |
| WO | WO 03/061663 | 7/2003 |
| WO | WO 03/091232 | 11/2003 |
| WO | WO 03/106482 | 11/2003 |
| WO | WO 04/006899 | 1/2004 |
| WO | WO 04/056748 | 7/2004 |
| WO | WO 04/076430 | 9/2004 |
| WO | WO 04/089350 | 9/2004 |
| WO | WO 04/020421 | 10/2004 |
| WO | WO2004/089350 | 10/2004 |
| WO | WO 07/009655 | 1/2007 |
| WO | WO 07/009656 | 1/2007 |
| WO | WO 08/058628 | 5/2008 |
| WO | WO 08/058630 | 5/2008 |
| WO | WO 08/058631 | 5/2008 |
| WO | WO 10/062861 | 6/2010 |
| WO | WO 2010/041268 | 9/2010 |
| WO | WO 11/137135 | 11/2011 |
| WO | WO 11/150286 | 12/2011 |
| WO | WO 12/064267 | 5/2012 |
| WO | WO 12/064268 | 5/2012 |
| WO | WO 13/063512 | 5/2013 |
| WO | WO 13/063526 | 5/2013 |
| WO | WO 2014/174066 | 10/2014 |
| WO | WO 2015/193788 | 12/2015 |

OTHER PUBLICATIONS

U.S. Appl. No. 15/134,583, filed Apr. 21, 2016, Bohlin et al.
U.S. Appl. No. 15/134,586, filed Apr. 21, 2016, Bohlin et al.
U.S. Appl. No. 15/449,645, filed Mar. 3, 2017, Gillberg et al.
U.S. Appl. No. 15/449,781, filed Mar. 3, 2017, Gillberg et al.
U.S. Appl. No. 15/449,779, filed Mar. 3, 2017, Gillberg et al.
U.S. Appl. No. 15/320,651, filed Dec. 20, 2016, Ando et al.
U.S. Appl. No. 15/320,621, filed Dec. 20, 2016, Ando et al.
AASLD: 2017 68th Annual Meeting of the American Association for the Study of Liver Diseases, Washington, DC, Oct. 20-24, 2017, (Abstract only).
Alonso et al., "Histologic pathology of the liver in progressive familial intrahepatic cholestasis," Journal of Pediatric Gastroenterology and Nutrition, 14: 128-133, 1994.
Alvarez, Fernando; "Treatments in chronic cholestasis in children." Ann. Nestlé (2008) 66 p. 127-135.
Balbach et al., "Pharmaceutical evaluation of early development candidates "the 100 mg-approach"," Int J Pharm, May 4, 2004, 275(1):1-12.
Billington et al., "Effects of bile salts on the plasma membranes of isolated rat hepatocytes," Bichem. J. 188: 321-327, 1980.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Caira, "Crystalline Polymorphism of Organic Compounds," in: Topics in Current Chemistry, Jan. 1998, 198:163-208.
Chen et al., "Bile salt export pump is dysregulated with altered farnesoid X receptor isoform expression in patients with hepatocelular carcinoma," Hepatologu, 57: 4, 1530-1541, 2013.
Chen et al., "Serum and urine metabolite profiling reveals potential biomarkers of human hepatocellular carcinoma," Molecular and Cellular Proteomics 10.7, 2011.

(56) References Cited

OTHER PUBLICATIONS

Faubion et al., "Toxic bile salts induce rodent hepatocyte apoptosis via direct activation of Fas," The Journal of Clinical Investigation, 103: 1, 137-145, 1999.
Forner et al., "Treatment of hepatocellular carcinoma," Critical Reviews in Oncology/Hematology, 2006, 60:89-98.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Search Report and Written Opinion for Application No. PCT/SE2017/050127, dated May 8, 2017, 16 pages.
International Search Report and Written Opinion for International Application No. PCT/EP2015/074573, dated Apr. 28, 2016, 11 pages.
Jansen et al., "Endogenous bile acids as carcinogens," Journal of Hepatology, 47, 434-435, 2007.
Knisely et al., "Hepatocellular Carcinoma in ten children under five years of age with bile salt export pump deficiency," Hepatology, 44: 2, 478-486, 2006.
Kurbegov et al., Biliary diversion for progressive familial intrahepatic cholestasis: Improved liver morphology and bile acid profile, Gastroenterology, 125: 4, 1227-1234, 2003.
Perez et al., "Bile-acid-induced cell injury and protection," World J Gastroenterol, 15: 25, 1677-1689, 2009.
Qiu et al., "Disruption of BSEP function in HepaRG cells alters bile acid disposition and is a susceptible factor to drug-induced cholestatic injury," Mol. Pharmaceutics, 13:4,, 2016 (Abstract only).
Rolo et al., "Bile acids affect liver mitochondrial bioenergetics: Possible relevance for cholestasis therapy," Toxocological Sciences, 57: 177-185, 2000.
Singhal et al., "Drug polymorphism and dosage form design: a practical perspective," Adv Drug Deliv Rev, Feb. 23, 2004, 56(3):335-347.
The ileal bile acid transport inhibitor A4250 decreases pruritus and serum bile acids in cholestatic liver diseases—an ongoing multiple dose, open-label, multicenter study, 2017 (Abstract only).
Wang et al., "Bile acid receptors and liver cancer," Curr. Pathobiol Rep, 1, 29-35, 2013.
Whitington et al., "Partial external diversion of bile for the treatment of intractable pruitus associated with intrahepatic cholestasis," Gastroenterology, 95: 1, 130-136, 1988 (Abstract only).
Woolbright et al., "Novel insight into mechanisms of cholestatic liver injury," World Journal of Gastroenterology, 18: 36, 4985-4993, 2012.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zhang et al., "Effect of bile duct ligation on bile acid composition in mouse serum and liver," Liver int, 32: 1, 58-69, 2012.
Zhang et al., Abcb11 deficiency induces cholestasis coupled to impaired B-Fatty acid oxidation in mice, Journal of biological chemistry, 287: 29, 24784-2479, 2012.
"A Long-Term, Open-Label Study of LUM001 With a Double-Blind, Placebo Controlled, Randomized Drug Withdrawal Period to Evaluate Safety and Efficacy in Children With Alagille Syndrome (Iconic)," Clinical Trials.gov, Jun. 9, 2014, retrieved Oct. 3, 2014, http://clinicaltrials.gov/ct2/show/NCT02160782?term=LUM001&rank=7, 4 pages.
"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.
"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.

"An Extension Study to Evaluate the Long-Term Safety and Durability of Effect of LUM001 in the Treatment of Cholestatic Liver Disease in Subjects With Alagille Syndrome (Imagine)," Clinical Trials.gov, Jan. 23, 2014, retrieved on Oct. 3, 2014, http://clinicaltrials.gov/ct2/show/NCT02047318?term=LUM001&rank=3, 3 pages.
"An Extension Study to Evaluate the Long-Term Safety and Durability of Effect of LUM001 in the Treatment of Cholestatic Liver Disease in Subjects With Alagille Syndrome (Imagine-II)," Clincal Trials.gov, Apr. 16, 2014, retrieved on Oct. 3, 2014, http://clinicaltrials.gov/ct2/show/NCT02117713?term=LUM001&rank=2, 3 pages.
"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
"EASL Clinical Practice Guidelines: Management of cholestatic liver diseases," European Assoc. for the Study of the Liver, Journal of Hepatology, 2009, 51:237-267.
"Evaluation of LUM001 in the Reduction of Pruritus in Alagille Syndrome (Itch)," Clinical Trials.gov, Feb. 5, 2014, retrieved on Oct. 3, 2014, http://clinicaltrials.gov/ct2/show/NCT02057692?term=LUM001&rank=5, 4 pages.
"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.
"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.
"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
"Open Label Study to Evaluate Efficacy and Long Term Safety of LUM001 in the Treatment of Cholestatic Liver Disease in Patients With Progressive Familial Intrahepatic Cholestasis (Indigo)," Clinical Trials.gov, Feb. 5, 2014, retrieved on Oct. 3, 2014, http://clinicaltrials.gov/ct2/show/NCT02057718?term=LUM001&rank=4, 3 pages.
"Open Label Study to Evaluate Safety and Efficacy of LUM001 in Patients With Primary Sclerosing Cholangitis (Cameo)," Clinical Trials.gov, Feb. 11, 2014, retrieved Oct. 3, 2014, http://clinicaltrials.gov/ct2/show/NCT02061540?term=LUM001&rank=6, 3 pages.
"Phase 2 Study to Evaluate LUM001 in Combination With Ursodeoxycholic Acid in Patients With Primary Biliary Cirrhosis (Clarity)," Clinical Trials.gov, Jul. 17, 2013, retrieved Oct. 3, 2014, http://clinicaltrials.gov/ct2/show/NCT01904058?term=LUM001&rank=8, 3 pages.
"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.
"Safety and Efficacy Study of LUM001 in the Treatment of Cholestatic Liver Disease in Patients With Alagille Syndrome (Imago)," Clinical Trials.gov, Jul. 16, 2013, http://clinicaltrials.gov/ct2/show/NCT01903460?term=LUM001&rank=1, 3 pages.
"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Alissa et al., "Invited Review: Update on Progressive Familial Intrahepatic Cholestasis," *Journal of Pediatric Gastroenterology and Nutrition*, 2008, 46:241-252.
American Diabetes Association, "Management of Dyslipidemia in Adults with Diabetes," Diabetes Care, Jan. 2003, 26(1).
Angulo, "Use of ursodeoxycholic acid in patients with liver disease," *Current Gastroenterology Reports*, Feb. 1, 2002, 4(1):37-44.
Artursson and Karlsson, "Corresslation Between Oral Drug Absorption in Humans and Apparent Drug Permeability Coefficients in

(56) References Cited

OTHER PUBLICATIONS

Human Intestinal Epithelial (Caco-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibito A4250 protects liver injury in mice," J. Hepatology, 2014, 60:S57.
Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Banker et al., "Modern Pharmaceutics, 3ed", Marcel Dekker, New York, 1996, pp. 451 and 596.
Bavin, "Polymorphism in Process Development," Chemistry and Industry, 527-529, 1989.
Board of Appeal of European Patent Office, Case No. T 077/08-3.3.01, dated May 24, 2011, 17 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Brunzell and Hokanson, "Dislipidemia of Central Obesity and Insulin Resistance," Diabetes Care, 1999, 22(Suppl. 3):C10-C13.
Byrn et al., "Pharmaceutical Solids: A Strategic Approach to Regulatory Considerations," Pharmaceutical Research, 1995, 12(7), pp. 945-954.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.
Chourasia et al., "Polysaccharides for colon targeted drug delivery," Drug Delivery, Academic Press, vol. 11, No. 2, Jan. 1, 2004, XP008060983.
Dashti et al., "A Phospholipidomic Analysis of All Defused Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," *Hepatology: Autoimmune, Cholestatic and Biliary Disease,* May 2010, 1645-1655.
Davit-Spraul et al., "Progressive familial intrahepatic cholestasis," *Orphanet Journal of Rare Diseases,* Jan. 2009, 4:1-12.
Dawson et al., "Bile acid transporters" J. Lipid Res. 2009, 50, 2340-2357.
DeFronzo et al., "Insuline resistance, a multisurfaced syndrome responsible for NIDDM, obesity, hypertension, dyslipidemia and atherosclerotic cardiovascular disease," Diabetes Care, 1991, 14:173-194.
Di Padova et al., "Double-blind placebo-controlled clinical trial of microporous chlestyramine in the treatment of intra-and extra-hepatic cholestasis: relationship between itching and serum bile acids," Methods Find Exp Clin Pharmacol., Dec. 1984, 6(12):773-776 (Abstract Only).
Dongiovanni et al., "Genetic Predisposition in NAFLD and NASH: Impact on Severity of Liver Disease and Response to Treatment," Curren Pharma Design, 2013, 19:5219-5238.
Espenshade and Hughes, "Regulation of Sterol Synthesis in Eukaryotes," Annu. Rev. Genet., 2007, 41:401-427.
Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS30D_Promotiondatasheet_09072008.
Extended European Search Report in European Application No. 11840392.2, dated Feb. 24, 2014, 7 pages.
Extended European Search Report in European Application No. 11840481.3, dated Feb. 13, 2014, 10 pages.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "The IBAT Inhibition by A3309—A Potential Mechanism for the Treatment of Constipation," Gastroenterology, 2010, 138(5), Supp 1, S-224.
Glasgov et al., "Compensatory enlargement of human athersclerotic coronary arteries," N Engl J. Med., May 1987, 316(22):1371-1375 (Abstract Only).
Govers et al., "Characterization of the adsorption of conjugated and unconjugated bile acids to insoluble, amorphous calcium phosphate", Journal of Lipid Research 35(5):741-748, 1994.
Hancock et al., "Molecular Mobility of amorphous pharmaceutical solids below their glass transition temperatures," 12(6): 799-806, 1995.
Heathcote, "Management of primary biliary cirrhosis," Hepatology, 2000, 31(4):1005-1013.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Huang et al., "Discovery of Potent, Nonsystemic Apical Sodium-Codependent Bile Acid Transporter Inhibitors (Part 2)," J. Med. Chem., 2005, 48:5853-5868.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for International Application No. PCT/SE2011/051335, dated Feb. 3, 2012, 12pages.
International Search Report and Written Opinion for International Application No. PCT/SE2011/051336, dated Feb. 22, 2012, 18 pages.
Ishibashi et al., "Hypercholesterolemia in low density lipoprotein receptor knockout mice and its reversal by adenovirus-mediated gene delivery", Journal of Clinical Investigation 92(2):883-893, 1993.
Jacquet et al., "Alagille Syndrome in Adult Patients: It is Never Too Late," *American Journal of Kidney Diseases,* May 2007, 49(5):705-709.
Korman et al., "Assessment of Activity in Chronic Active Liver Disease," New England Journal of Medicine, 2010, 290(25):1399-1402.
Kumar and Tandon, "Use of ursodeoxycholic acid in liver diseases," J. Gastroenterology and Hepatology, 2001, 16:3-14.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.
Lewis et al., "Effects of 2164U90 on ileal bile acid adsorption and serum cholesterol in rats and mice", Journal of Lipid Research 36(5):1098-1105, 1995.
Ling, "Congenital cholestatic syndromes: What happens when children grow up?," Can J Gastroenterol, Nov. 11, 2007, 21(11):743-751.
Longo et al., "Hyperlipidemia in chronic cholestatic liver disease," Curr. Treat. Options Gastrenterol., 2001, 4:111-114.

(56) References Cited

OTHER PUBLICATIONS

Lykavieris et al., "Outcome of liver disease in children with Alagille syndrome: a study of 163 patients," *Gut,* 2001, 49:431-435.

MerckManuals.com', "Obesity," 2008, Merch Manual for Health Care Professionals, Section-Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.

Morissette et al., "High-throughput crystallization: polymorphs, salts, co-crystals and solvates of pharmaceutical solids," Advanced Drug Delivery Reviews, 2004, 56:275-300.

Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.

Parker et al., "Molecular mechanisms underlying bile acid-stimulated glucagon-like peptide-1 secretion," British J. Pharmacology, 2012, 165:414-423.

Patani et al., "Bioisosterism: A Rational Approach in Drug Design," Chem Rev, 1996, 96:3147-3176.

Plump et al., "Severe hypercholesterolemia and atherosclerosis in apolipoprotein E-deficient mice created by homologous recombination in ES cells", Cell (71):343-353, 1992.

Podesta et al., "Treatment of pruritus of primary biliary cirrhosis with rifampin," Dig. Dis. Sci, 1991, 36(2):216-220.

Poupon et al., "Chronic Cholestatic Disease," J. Hepatology, 2000, 32(1):12-140.

Report filed at oral proceedings before opposition division, GMS-CFEP-2007-20, "Filtration and Drying Study on Amorphous and Form IV Atorvastatin Calcium," 2007.

Report EC20082069.02.01 dated Feb. 2009, filed with appellant's letter of Apr. 26, 2011.

Schiller, "Review article: the therapy of constipation", Alimentary Pharmacology and Therapeutics 15(6):749-763, 2001.

Shah et al., "Role of Caco-2 Cell Monolayers in Prediction of Intestinal Drug Absorbtion," Biotechnol. Prog., 2006, 22:186-198.

Shang et al., "Colesevelam improves insulin resistance in a diet-induced obesity (F-DIO) rat model by increasing the release of GLP-1," Am J. Physiol Gastrointest Liver Physiol, 2010, 298:G419-G424.

Sorrentino et al., "A Clinical-Morphological Study on Cholestatic Presentation of Nonalcoholic Fatty Liver Disease," Digestive Disease and Sciences, Jun. 2005, 50(6):1130-1135.

Sprong et al., "Dietary Calcium Phosphate Promotes Listeria monosytogenes colonization and translocation in rats red diets containing corn oil but not milk fat1", J. Nutrition (US) 132(6):1269-1274, 2002.

Staels and Kuipers, "Bile Acid Sequestrants and the Treatment of Type 2 *Diabetes mellitus,*" Drugs, 2007, 67(10):1383-1392.

Stein, "Managing Dyslipidemia in the High-Risk Patient," Am J. Cardiol., 2002, 89:50-57.

Tanaka et al., "Genetic and Familial considerations of Primary Binary Cirrhosis," Am. J. Gastroenterology, 2001, 96(1): 8-15.

Tollefson et al., "A novel class of apical sodium co-dependent bile acid transporter inhibitors: the 1,2-Benzothiazepines", Bioorganic and Medicinal Chemistry Letters 12:3727-3730, 2003.

Tremont et al., "Discovery of Potent, Nonsystemic Apical Sodium-Codependent Bile Acid Transporter Inhibitors (Part 1)," J. Med. Chem, 2005, 48:5837-5852.

Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.

Van Tilberg et al., "Na+-dependent bile acid transport in the ileum: the balance between diarrhea and constipation", Gastroenterology 98(1):25-32, 1989.

Vippagunta et al., "Crystalline solids", Advanced Drug Delivery Reviews 48:3-26, 2001.

Watts and Ilium, "Colonic Drug Delivery," Drug Development and Industrial Pharmacy, 1997, 23(9):893-913.

Welberg et al., "Calcium and the prevention of colon cancer", Scandinavian J. Gasteroenterology Suppl. 188:52-59, 1991.

Williams et al., Foye's Principles of Medicinal Chemistry, 5th Edition, 2002, 59-63.

Wolff, "Burger's Medicinal Chemistry, 5ed, Part I", John Wiley & Sons, 1995, pp. 975-977.

Das & Kar., Non alcoholic steatohepatitis. JAPI. 53:, Mar. 2005.

Berazs et al., Nor-ursodeoxycholic acid reverses hepatocyte-specific nemo-dependnt steatohepatitis. Gut, 2011: 60: 387-396.

Carulli et al, "Review article: effect of bile salt pool composition on hepatic and biliary functions," Aliment. Phannacol. Ther. 2000, vol. 14, suppl. 2, p. 14-18.

Islam and Di Baise, "Bile Acids: An underrecognized and underappreciated cause of chronic diarrhea," Pract. Gastroenterol. 2012, vol. 36(10), p. 32-44.

Jacobsen et al., "Effect of enterocoated cholestyramine on bowel habit after ileal resection: a double blind crossover study," Br. Med. J. 1985, vol. 290, p. 1315-1318.

Marzorati et al, "A novel hypromellose capsule, with acid resistance properties, permits the targeted delivery of acid-sensitive products to the intestine," LWT-Food Sci. Techno.l 2015, vol. 60, p. 544-551.

Pattni and Walters, "Recent advances in the understanding of bile acid malabsorption," Br. Med. Bull. 2009, vol. 92, p. 79-93.

Possemiers et al, "PCR-DGGE-based quantification of stability of the microbial community in a simulator of the human intestinal microbial ecosystem," FEMS Microbiol. Ecol. 2004, vol. 49, p. 495-507.

Sinha and Kumria, "Microbially triggered drug delivery to the colon," Eur. J. Phann. Sci. 2003, vol. 18, p. 3-18.

Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.

International Search Report and Written Opinion for Application No. PCT/SE2017/050128, dated May 8, 2017, 16 pages.

International Search Report and Written Opinion for Application No. PCT/SE2017/050126, dated Apr. 24, 2017, 27 pages.

Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.

International Search Report, Application No. PCT/JP2015/068240, dated Sep. 15, 2015.

Anakk et al., "Bile acids activate YAP to promote liver carcinogenesis," Cell Rep., Nov. 27, 2013, 5(4):1060-1069.

Angulo et al., "Independent Predictors of Liver Fibrosis in Patients With Nonalcoholic Steatohepatitis," Hepatology, Dec. 1999, 30(6): 1356-1362.

Brunt et al., "Nonalcoholic Steatohepatitis: A Proposal for Grading and Staging the Histological Lesions," American Journal of Gastroenterology, Sep. 1999, 94(9): 2467-2474.

Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.

Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.

hepc.liverfoundation.org' [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.

Hollands et al., "Ileal exclusion for Byler's disease: an alternative surgical approach with promising early results for pruritus,"Journal of Pediatric Surgery, Feb. 1988, 33(2): 220-224.

Jiang et al., "Non alcoholic steatohepatitis a precursor for hepatocellular carcinoma development," World Journal of Gastroenterology: WJG, Nov. 28, 2014, 20(44):16464-16473.

(56) References Cited

OTHER PUBLICATIONS

Mouzaki and Allard, "Non-alcoholic steatohepatitis: the therapeutic challenge of a global epidemic," Annals of Gastroenterology, 2012, 25: 207-217.

Perumpail et al., "Clinical epidemiology and disease burden of nonalcoholic fatty liver disease," World Journal of Gastroenterology, Dec. 2017, 23(47): 8263-8276.

Satapathy and Sanyal, "Epidemiology and Natural History of Non-alcoholic Fatty Liver Disease," Seminars in Liver Disease, Aug. 2015, 35(3): 221-235.

Scheuer, "Primary Biliary Cirrhosis," Proc. R. Soc. Med., Dec. 1967, 60:1257-1260.

Sun et al., "Bile acids promote diethylnitrosamine-induced hepatocellular carcinoma via increased inflammatory signaling," American Journal of Physiology-Gastrointestinal and Liver Physiology, May 5, 2016, 311(1):G91-104.

Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.

Xie et al., "Dysregulated hepatic bile acids collaboratively promote liver carcinogenesis," Int J Cancer, Oct. 15, 2016, 139(8):1764-1775.

CRYSTAL MODIFICATIONS OF ELOBIXIBAT

CROSS REFERENCE TO RELATED APPLICATION

This application is a National Stage Application under 35 U.S.C. § 371 and claims the benefit of International Application No. PCT/EP2015/074573, filed Oct. 23, 2015, which claims priority to European Application No. 14190290.8, filed Oct. 24, 2014, the disclosures of which are incorporated herein by reference in their entireties.

The present invention relates to crystal modifications of N-{(2R)-2-[({[3,3-dibutyl-7-(methylthio)-1,1-dioxido-5-phenyl-2,3,4,5-tetrahydro-1,5-benzothiazepin-8-yl]oxy}acetyl)amino]-2-phenylethanolyl}-glycine (elobixibat).

BACKGROUND

WO 02/50051 discloses the compound 1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine (elobixibat; IUPAC name: N-{(2R)-2-[({[3,3-dibutyl-7-(methylthio)-1,1-di-oxido-5-phenyl-2,3,4,5-tetrahydro-1,5-benzothiazepin-8-yl]oxy}acetyl)amino]-2-phenylethanolyl}glycine). This compound is an ileal bile acid transporter (IBAT) inhibitor, which can be used in the treatment or prevention of diseases such as dyslipidemia, constipation, diabetes and liver diseases. According to the experimental section of WO 02/50051, the last synthetic step in the preparation of elobixibat consists of the hydrolysis of a tert-butoxyl ester under acidic conditions. The crude compound was obtained by evaporation of the reaction mixture under reduced pressure and purification of the residue by preparative HPLC using acetonitrile/ammonium acetate buffer (50:50) as eluent (Example 43). After freeze drying the product, no crystalline material was identified.

It would be desirable to discover forms of elobixibat that are sufficiently robust to be suitable for formulation as a pharmaceutical.

Various crystal modifications may have disadvantages including residual solvents, a variable degree of crystallinity and difficulties in handling and formulating. Thus, there is a need for crystal modifications of elobixibat having improved properties with respect to stability, bulk handling and solubility. It is therefore an object of the present invention to provide a stable crystal modification of elobixibat with good crystallinity and other formulation properties.

SUMMARY OF THE INVENTION

The invention provides various crystal modifications of elobixibat. This invention is based in part on the discovery that elobixibat tends to form highly crystalline solvated structures with many solvents. As seen in the examples below, a number of the crystal modifications form crystalline ansolvates when the solvent is removed from the crystal. Several of these crystals can then form hydrates, following exposure to a sufficiently humid environment. It is surprising that these crystal modifications contain a substantially stoichiometric amount of solvate in view of their ability to lose and regain solvate molecules without dissolution and recrystallization.

In one aspect, the crystal modification is a crystalline form of elobixibat that is capable of containing or actually contains a substantially stoichiometric amount of water. Preferably, the substantially stoichiometric amount of water is not one mole per mole of elobixibat. A substantially stoichiometric amount of water is an amount that is within 15 mol % of a whole number value. Thus, for example, a dihydrate includes 1.7-2.3 moles of water associated with each mole of elobixibat in a crystal. The amount of water calculated herein excludes water adsorbed to the surface of the crystal. The invention also includes anhydrates of elobixibat.

The invention further provides methods of treating a condition described herein and use of the crystal modifications described herein in treating a condition described herein and in the manufacture of a medicament for the treatment of a condition described herein.

DETAILED DESCRIPTION OF THE INVENTION

Figure 1:
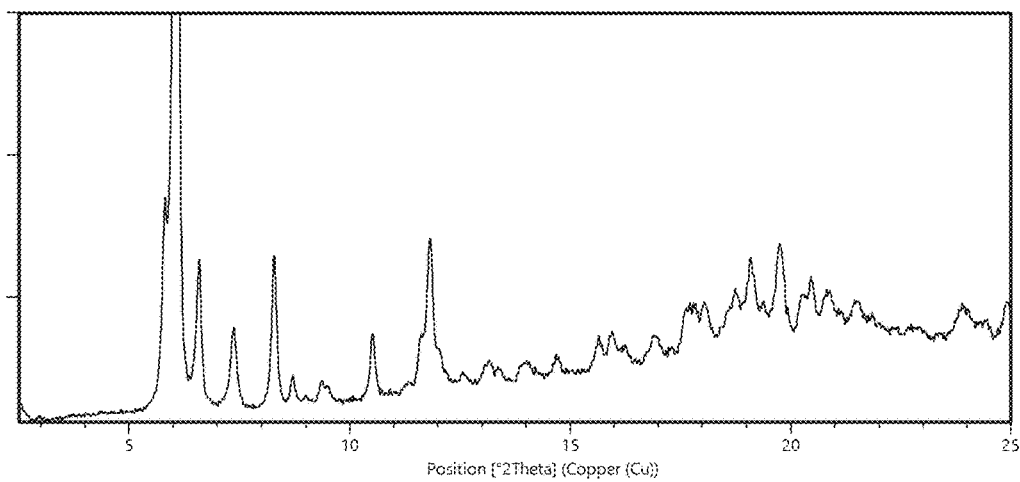
FIG. 1 shows the X-ray powder diffractogram of crystal modification F produced from methyl isobutyl ketone.

The invention described herein relates to crystal modifications that were discovered in extensive studies on elobixibat. While not wishing to be bound by theory, it is believed that crystalline forms of elobixibat can be formed from a variety of solvents possessing at least some polar character. Again not wishing to be bound by theory, it is believed that elobixibat forms crystal structures containing occupied or partially occupied void volumes, where the solvent molecules reside. The voids are in many of these crystals unusual in that they hold substantially stoichiometric amount of solvate (e.g., hydrate) molecules, yet the solvate molecules can be removed and replaced without dissolution and recrystallization of the crystals. It is advantageous to contain substantially stoichiometric amounts of water, as the water content of crystals remains substantially constant even with changes in relative humidity. In certain embodiments, the water content remains substantially constant at RH greater than 20%, 30%, 40% or more. In other embodiments, the water content remains substantially constant at RH less than 20% or 10%.

In one aspect, the invention relates to a crystalline form of elobixibat, where the form includes void volumes that are capable of containing a substantially stoichiometric amount of water, such as under conditions of 10% RH and 20° C., 40% RH and 20° C., 58% RH and 20° C., 80% RH and 20° C., or 75% RH and 40° C. The invention includes both the hydrate and anhydrate forms of the relevant crystals. Preferably, the substantially stoichiometric amount of water is not one mole per mole of elobixibat (e.g., 0.7-1.3 mol, 0.8-1.2 mol or 0.9-1.1 moles of water per mole of elobixibat). A substantially stoichiometric amount of water is an amount that is within 15 mol % (e.g., 10 mol %, 5 mol %, 2.5 mol %) of a whole number value. Thus, for example, a dihydrate includes 1.7-2.3, 1.8-2.2, 1.9-2.1 or 1.95-2.05 moles of water associated with each mole of elobixibat in a crystal. For an anhydrate, there is less than 0.15 moles, less than 0.10 moles or even less than 0.05 or 0.025 moles associated with each mole of elobixibat. The amount of water calculated herein excludes water adsorbed to the surface of the crystal. Void volumes as used herein, refer to channels, layers or more or less isolated voids in the crystal structure.

In certain embodiments, the invention includes a crystalline anhydrate of elobixibat, where the anhydrate is stable at a relative humidity (RH) of 10% or less or 20% or less at a temperature of 20° C. Such anhydrates can be stable under these conditions for at least 1 hour, 1 day, 1 month, 3 months, 6 months, 1 year, 2 years, 3 years or longer. It is advantageous for certain anhydrates to be stable for these periods under different storage conditions, such as 40% RH and 20° C., 58% RH and 20° C., 80% RH and 20° C., or 75% RH and 40° C. Anhydrates stable at 10% RH (e.g., at 20° C. or 40° C.) are particularly suitable for Zone III conditions (hot/dry) or in formulations containing drying agents (e.g., silica gel, calcium sulfate, calcium chloride, calcium phosphate, sodium chloride, sodium bicarbonate, sodium sulfate, sodium phosphate, montmorillonite, molecular sieves (beads or powdered), alumina, titania, zirconia, and sodium pyrophosphate), whereas anhydrates stable at 40% RH and above are suitable for Zone I (temperate), II (subtropical) and IV (hot/humid) conditions.

Stability can be assessed as physical stability, chemical stability or both. Chemical stability refers to the molecule (i.e., elobixibat) not undergoing reaction to a new molecule. Physical stability refers to the crystal structure not changing over time, which can be measured by one or more of the techniques discussed herein such as XPRD, and optionally complemented by DVS, TGA and DSC.

Figure 2:
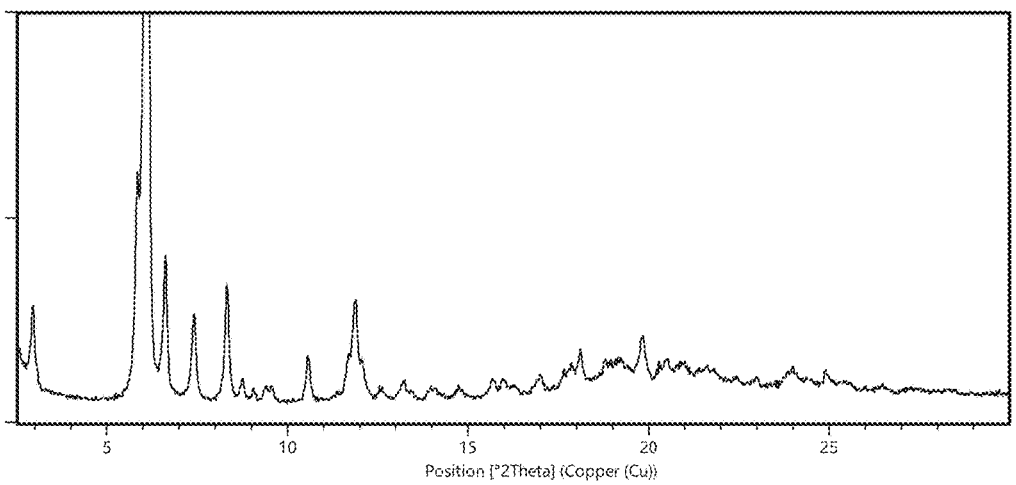
FIG. 2 shows the X-ray powder diffractogram of crystal modification F produced from ethyl acetate.

In one embodiment, the crystalline anhydrate is crystal modification F having an X-ray powder diffraction (XRPD) pattern, obtained with CuKα1-radiation, with at least specific peaks at °2θ positions 6.1±0.2 and/or 5.9±0.2. In certain embodiments, the invention relates to crystal modification F having an XRPD pattern, obtained with CuKα1-radiation, with specific peaks at °2θ positions 6.1±0.2 and 5.9±0.2 and one or more of the characteristic peaks: 6.6±0.2, 8.3±0.2, and 11.9±0.2. In a more particular embodiment, the invention relates to crystal modification F having an XRPD pattern, obtained with CuKα1-radiation, with specific peaks at °2θ positions 6.1±0.2, 5.9±0.2, 6.6±0.2, 8.3±0.2, and 11.9±0.2. In a further embodiment, the invention relates to crystal modification F having an XRPD pattern, obtained with CuKα1-radiation, with characteristic peaks at °2θ positions 6.1±0.2, 5.9±0.2, 6.6±0.2, 8.3±0.2, and 11.9±0.2, and one or more of 7.4±0.2, 10.6±0.2, 11.7±0.2, 19.2±0.2, and 19.8±0.2. In a yet more particular embodiment, the invention relates to crystal modification F having an XRPD pattern, obtained with CuKα1-radiation, substantially as shown in FIG. 1 or FIG. 2.

Figure 3:
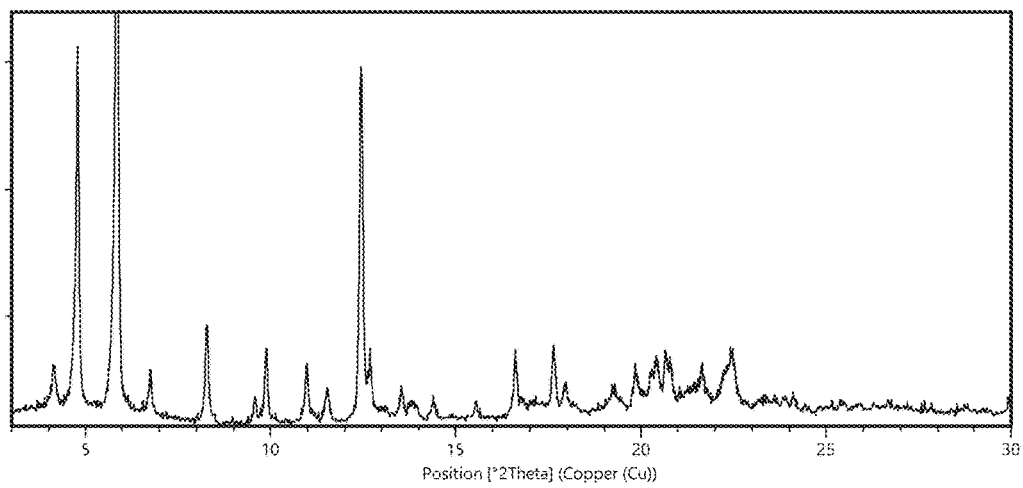
FIG. 3 shows the X-ray powder diffractogram of crystal modification C produced from acetone:water 1:1 v/v.
Figure 4:
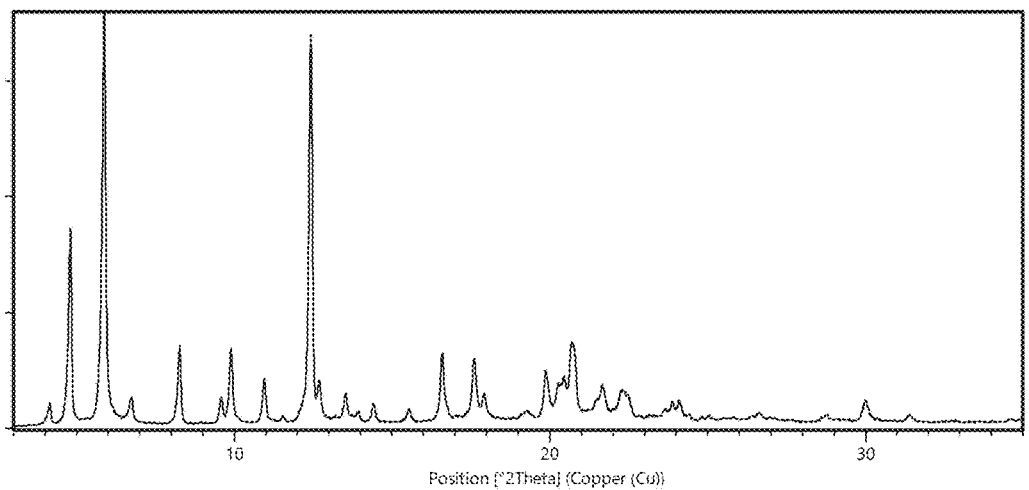
FIG. 4 shows the X-ray powder diffractogram of crystal modification C produced from ethyl acetate.

In one embodiment, the crystalline anhydrate is crystal modification C having an X-ray powder diffraction (XRPD) pattern, obtained with CuKα1-radiation, with at least specific peaks at °2θ positions 12.4±0.2 and/or 5.8±0.2. In certain embodiments, the invention relates to crystal modification C having an XRPD pattern, obtained with CuKα1-radiation, with specific peaks at °2θ positions 12.4±0.2 and 5.8±0.2 and one or more of the characteristic peaks: 4.8±0.2, 8.2±0.2, 9.9±0.2, 10.9±0.2, 16.6±0.2, 19.8±0.2 and 20.6±0.2. In a more particular embodiment, the invention relates to crystal modification C having an XRPD pattern, obtained with CuKα1-radiation, with specific peaks at °2θ positions 12.4±0.2, 5.8±0.2, 4.8±0.2, 8.2±0.2, 9.9±0.2, 10.9±0.2, 16.6±0.2, 19.8±0.2 and 20.6±0.2. In a further embodiment, the invention relates to crystal modification C having an XRPD pattern, obtained with CuKα1-radiation, with characteristic peaks at °2θ positions 12.4±0.2, 5.8±0.2, 4.8±0.2, 8.2±0.2, 9.9±0.2, 10.9±0.2, 16.6±0.2, 19.8±0.2 and 20.6±0.2, and one or more of 4.1±0.2, 6.7±0.2, 9.5±0.2, 12.6±0.2, and 20.7±0.2. In a yet more particular embodiment, the invention relates to crystal modification C having an XRPD pattern, obtained with CuKα1-radiation, substantially as shown in FIG. 3 or FIG. 4.

Figure 5:
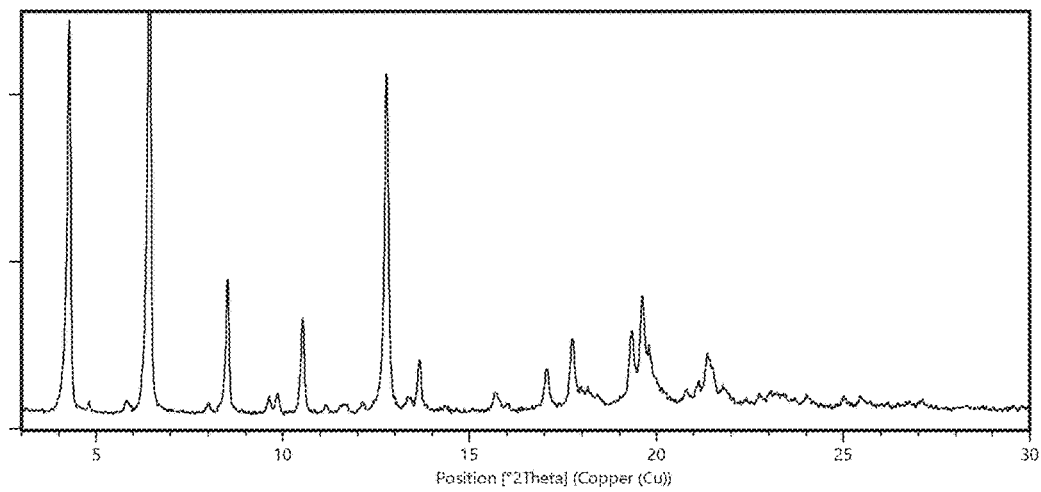
FIG. 5 shows the X-ray powder diffractogram of crystal modification L.

In one embodiment, the crystalline anhydrate is crystal modification L having an X-ray powder diffraction (XRPD) pattern, obtained with CuKα1-radiation, with at least specific peaks at °2θ positions 6.4±0.2 and/or 12.7±0.2. In certain embodiments, the invention relates to crystal modification L having an XRPD pattern, obtained with CuKα1-radiation, with specific peaks at °2θ positions 6.4±0.2 and 12.7±0.2 and one or more of the characteristic peaks: 4.2±0.2, 8.5±0.2, 10.5±0.2, 19.3±0.2 and 19.5±0.2. In a more particular embodiment, the invention relates to crystal modification L having an XRPD pattern, obtained with CuKα1-radiation, with specific peaks at °2θ positions 6.4±0.2, 12.7±0.2, 4.2±0.2, 8.5±0.2, 10.5±0.2, 19.3±0.2 and 19.5±0.2. In a further embodiment, the invention relates to crystal modification L having an XRPD pattern, obtained with CuKα1-radiation, with characteristic peaks at °2θ positions 6.4±0.2, 12.7±0.2, 4.2±0.2, 8.5±0.2, 10.5±0.2, 19.3±0.2 and 19.5±0.2, and one or more of 4.8±0.2, 5.9±0.2, 12.1±0.2, 12.4±0.2, 13.3±0.2, 13.6±0.2, 17.7±0.2, 19.9±0.2 and 21.4±0.2. In a yet more particular embodiment, the invention relates to crystal modification L having an XRPD pattern, obtained with CuKα1-radiation, substantially as shown in FIG. 5.

In a second aspect, the invention includes a crystalline dihydrate of elobixibat. Preferably, the dihydrate includes 1.7-2.3, 1.8-2.2, 1.9-2.1 or 1.95-2.05 moles of water associated with a crystal per mole of elobixibat. The amount of water calculated herein excludes water adsorbed to the surface of the crystal.

In one embodiment, the dihydrate is stable when in contact with water (e.g., a solution where water is the solvent). Such dihydrates may also or alternatively be stable in a saturated or nearly saturated atmosphere (i.e., 90%, 95%, 100% RH). Such dihydrates may be stable at temperatures of 20° C., 40° C., 60° C. or even 75° C. Stability can exist for a period of 1 day, 1 week, 1 month, 3 months, 6 months, 1 year, 2 years, 3 years or longer. In certain embodiments, the dihydrate is also stable at RH as low as 60%, 40% or even 20% for periods of 1 day, 1 week, 1 month, 3 months, 6 months, 1 year, 2 years, 3 years or longer, at temperatures of 20° C., 40° C., 60° C. or even 75° C.

In another embodiment, which may have a stability as indicated above, a dihydrate can be crystallized directly from slurry. In certain embodiments, crystallization can occur following synthesis of elobixibat without purification. Exemplary conditions include crystallization with 1:1 volume mixtures of methanol or 2-propanol and water at 5° C. Advantages of such direct crystallization include easier purification and less difficult separation, with an associated lower risk of residual solvents.

In one embodiment, the crystalline dihydrate is crystal modification N or E having an X-ray powder diffraction (XRPD) pattern, obtained with CuKα1-radiation, with at least specific peaks at °2θ positions 6.1±0.2 and/or 12.0±0.4.

Figure 6:
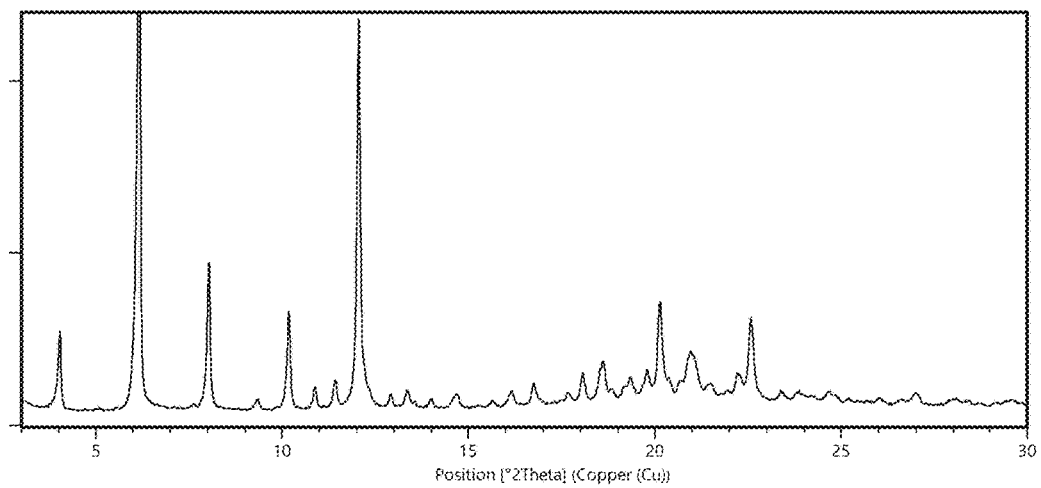
FIG. 6 shows the X-ray powder diffractogram of crystal modification N.

In embodiments where the dihydrate is crystal modification N, the XRPD pattern, obtained with CuKα1-radiation, has specific peaks at °2θ positions 6.1±0.2, 8.0±0.2 and 12.0±0.2; in certain embodiments, these are the most significant three peaks. In a particular embodiment, the invention relates to crystal modification N having an XRPD pattern, obtained with CuKα1-radiation, with specific peaks at °2θ positions 6.1±0.2, 8.0±0.2 and 12.0±0.2 and one or more of the characteristic peaks: 4.0±0.2, 10.1±0.2, 20.1±0.2 and 21.0±0.2. In a more particular embodiment, the invention relates to crystal modification N having an XRPD pattern, obtained with CuKα1-radiation, with specific peaks at °2θ positions 6.1±0.2, 8.0±0.2, 12.0±0.2, 4.0±0.2, 10.1±0.2, 20.1±0.2 and 21.0±0.2. In a further embodiment, the invention relates to crystal modification N having an XRPD pattern, obtained with CuKα1-radiation, with characteristic peaks at °2θ positions 6.1±0.2, 8.0±0.2, 12.0±0.2, 4.0±0.2, 10.1±0.2, 20.1±0.2 and 21.0±0.2, and one or more of 10.8±0.2, 11.4±0.2, 13.3±0.2, 18.0±0.2, 18.5±0.2 and 19.7±0.2. In a yet more particular embodiment, the invention relates to crystal modification N having an XRPD pattern, obtained with CuKα1-radiation, substantially as shown in FIG. 6.

Figure 7:
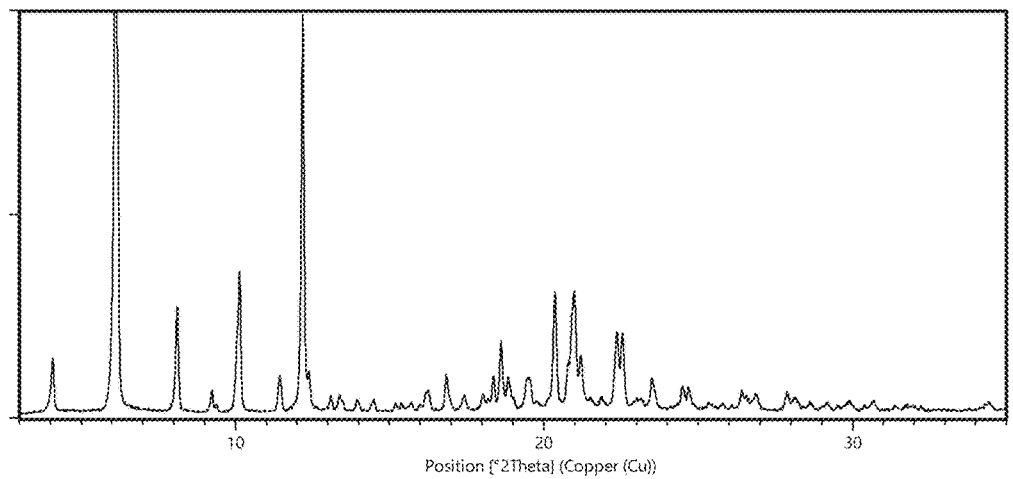
FIG. 7 shows the X-ray powder diffractogram of crystal modification E.

In embodiments where the dihydrate is crystal modification E, the XRPD pattern, obtained with CuKα1-radiation, has specific peaks at °2θ positions 6.1±0.2, 12.1±0.2 and 20.9±0.2; in certain embodiments, these are the most significant three peaks. In a particular embodiment, the invention relates to crystal modification E having an XRPD pattern, obtained with CuKα1-radiation, with specific peaks at °2θ positions 6.1±0.2, 12.1±0.2 and 20.9±0.2 and one or more of the characteristic peaks: 8.1±0.2, 10.1±0.2, 11.4±0.2, 22.3±0.2 and 22.5±0.2. In a more particular embodiment, the invention relates to crystal modification E having an XRPD pattern, obtained with CuKα1-radiation, with specific peaks at °2θ positions 6.1±0.2, 12.1±0.2, 20.9±0.2, 8.1±0.2, 10.1±0.2, 11.4±0.2, 22.3±0.2 and 22.5±0.2. In a further embodiment, the invention relates to crystal modification E having an XRPD pattern, obtained with CuKα1-radiation, with characteristic peaks at °2θ positions 6.1±0.2, 12.1±0.2, 20.9±0.2, 8.1±0.2, 10.1±0.2, 11.4±0.2, 22.3±0.2 and 22.5±0.2, and one or more of 4.0±0.2, 18.6±0.2, 19.4±0.2, 21.1±0.2. In a yet more particular embodiment, the invention relates to crystal modification E having an XRPD pattern, obtained with CuKα1-radiation, substantially as shown in FIG. 7.

The crystal modifications described above may advantageously include one or more of the following features, such as with respect to amorphous material: lower hygroscopicity, higher chemical stability, higher physical stability, improved ability to process into a formulation, reduced risk of residual solvent, improved ability to manufacture from crude synthesized elobixibat, and reproducible solubility. Many of these properties are highly relevant to compounds that are to be used in pharmaceutical preparations, where each formulation containing the active pharmaceutical ingredient should have the same pharmacological properties.

Elobixibat is an ileal bile acid transporter (IBAT) inhibitor. The ileal bile acid transporter (IBAT) is the main mechanism for re-absorption of bile acids from the GI tract. Partial or full blockade of that IBAT mechanism will result in lower concentration of bile acids in the small bowel wall, portal vein, liver parenchyma, intrahepatic biliary tree, and extrahepatic biliary tree, including the gall bladder. Diseases which may benefit from partial or full blockade of the IBAT mechanism may be those having, as a primary pathophysiological defect, symptoms of excessive concentration of bile acids in serum and in the above organs.

Thus, in another aspect, the invention also relates to crystal modifications of elobixibat described herein for use in therapy.

Crystal modifications of elobixibat described herein are useful in the prophylaxis or treatment of hypercholesterolemia, dyslipidemia, metabolic syndrome, obesity, disorders of fatty acid metabolism, glucose utilization disorders, disorders in which insulin resistance is involved, type 1 and type 2 diabetes mellitus, liver diseases, diarrhoea during therapy comprising an IBAT inhibitor compound, constipation including chronic constipation, e.g. functional constipation, including chronic idiopathic constipation (CIC) and constipation predominant irritable bowel syndrome (IBS-C). Treatment and prophylaxis of constipation is described in WO 2004/089350.

Further potential diseases to be treated with the crystal modifications of elobixibat described herein are selected from the group consisting of liver parenchyma, inherited metabolic disorders of the liver, Byler syndrome, primary defects of bile acid (BA) synthesis such as cerebrotendinous xanthomatosis, secondary defects such as Zellweger's syndrome, neonatal hepatitis, cystic fibrosis (manifestations in the liver), ALGS (Alagilles syndrome), progressive familial intrahepatic cholestasis (PFIC), autoimmune hepatitis, primary biliary cirrhosis (PBC), liver fibrosis, non-alcoholic fatty liver disease, NAFLD/NASH, portal hypertension, general cholestasis such as in jaundice due to drugs or during pregnancy, intra- and extrahepatic cholestasis such as hereditary forms of cholestasis such as PFIC1, primary sclerosing cholangitis (PSC), gall stones and choledocholithiasis, malignancy causing obstruction of the biliary tree, symptoms (scratching, pruritus) due to cholestasis/jaundice, pancreatitis, chronic autoimmune liver disease leading to progressive cholestasis, pruritus of cholestatic liver disease and disease states associated with hyperlipidaemic conditions.

Other diseases to be treated with the crystal modifications of elobixibat described herein are selected from the group consisting of hepatic disorders and conditions related thereto, fatty liver, hepatic steatosis, non-alcoholic steatohepatitis (NASH), alcoholic hepatitis, acute fatty liver, fatty liver of pregnancy, drug-induced hepatitis, iron overload disorders, hepatic fibrosis, hepatic cirrhosis, hepatoma, viral hepatitis and problems in relation to tumours and neoplasmas of the liver, of the biliary tract and of the pancreas.

Thus, in one embodiment, the invention relates to crystal modifications of elobixibat described herein for use in the treatment and/or prophylaxis of a disease or disorder as listed above.

In another embodiment, the invention relates to the use of crystal modifications of elobixibat described herein in the manufacture of a medicament for the treatment and/or prophylaxis of a disease or disorder as listed above.

In yet another embodiment, the invention relates to a method of treatment and/or prophylaxis of a disease or disorder as listed above in a warm-blooded animal, comprising administering an affective amount of crystal modifications of elobixibat described herein to a warm-blooded animal in need of such treatment and/or prophylaxis.

Another aspect of the invention relates to a pharmaceutical composition comprising an effective amount of crystal modifications of elobixibat described herein, in association with a pharmaceutically acceptable diluent or carrier.

Yet another aspect of the invention relates to the use of crystal modifications of elobixibat described herein in the preparation of a pharmaceutical composition, comprising admixing the crystal modification with a pharmaceutically acceptable diluent or carrier.

The pharmaceutical composition may further comprise at least one other active substance, such as an active substance selected from an IBAT inhibitor; an enteroendocrine peptide or enhancer thereof; a dipeptidyl peptidase-IV inhibitor; a biguanidine; an incretin mimetic; a thiazolidinone; a PPAR agonist; a HMG Co-A reductase inhibitor; a bile acid binder; a TGR5 receptor modulator; a member of the prostone class of compounds; a guanylate cyclase C agonist; a 5-HT4 serotonin agonist; or a pharmaceutically acceptable salt of any one these active substances. Examples of such combinations are also described in WO2012/064268.

Crystal modifications of elobixibat will normally be administered to a warm-blooded animal at a unit dose within the range of 5 to 5000 mg per square meter body area, i.e. approximately 0.1 to 100 mg/kg or 0.01 to 50 mg/kg, and this normally provides a therapeutically-effective dose. A unit dose form, such as a tablet or capsule, will usually contain about 1 to 250 mg of active ingredient, such as about 1 to 100 mg, or about 5 to 50 mg, e.g. about 1 to 20 mg. The daily dose can be administered as a single dose or divided into one, two, three or more unit doses. An orally administered daily dose of an IBAT inhibitor is preferably within 0.1 to 1000 mg, more preferably 1 to 100 mg, such as 5 to 15 mg.

The dosage required for the therapeutic or prophylactic treatment will depend on the route of administration, the severity of the disease, the age and weight of the patient and other factors normally considered by the attending physician when determining the individual regimen and dosage levels appropriate for a particular patient.

Definitions

The term "crystal modification" refers to a crystalline solid phase of an organic compound. A crystal modification can be either a solvate or an ansolvate.

The term "solvate" refers to a crystalline solid phase of an organic compound, which has solvent molecules incorporated into its crystal structure. A "hydrate" is a solvate wherein the solvent is water.

The term "slurry" refers to a saturated solution to which an overshoot of solid is added, thereby forming a mixture of solid and saturated solution, a "slurry".

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

When reference is made herein to a crystalline compound, preferably the crystallinity as estimated from X-ray powder diffraction data is greater than about 70%, such as greater than about 80%, particularly greater than about 90%, more particularly greater than about 95%. In embodiments of the invention, the degree of crystallinity as estimated by X-ray powder diffraction data is greater than about 98%, preferably greater than about 99%, wherein the % crystallinity refers to the percentage by weight of the total sample mass which is crystalline.

Preferably a crystal modification according to the invention is substantially free from other crystal modifications of the compound. Preferably, the described crystal modifications of elobixibat includes less than, for example, 20%, 15%, 10%, 5%, 3%, or particularly, less than 1% by weight of other crystal modifications of elobixibat. Thus, preferably, the solid phase purity of the described crystal modifications of elobixibat is >80%, >85%, >90%, >95%, >97%, or particularly >99%.

The invention will now be described by the following examples which do not limit the invention in any respect. All cited documents and references are incorporated by reference.

EXPERIMENTAL METHODS

X-Ray Powder Diffraction (XRPD) Analysis

Dry samples were lightly ground in an agate mortar, if needed, and were then smeared out on a sample holder. Slurry samples were added to the sample holder as wet and were analyzed both wet and dry. XRPD data were collected on a cut Silicon Zero Background Holder (ZBH) or on a Porous Alumina Filter Sample Holder, using a PANalytical X'Pert Pro diffractometer, equipped with an X'celerator or a PIXcel detector. The sample was spun during analysis and Cu-radiation was used. The following experimental settings were used:

Tube tension and current: 40 kV, 50 mA
Wavelength alpha1 (CuKα1): 1.5406 Å
Wavelength alpha2 (CuKα2): 1.5444 Å
Wavelength alpha1 and alpha2 mean (CuKα): 1.5418 Å
Start angle [2 theta]: 1-4°
End angle [2 theta]: 30-40°
Analysis time: 50 s ("1 min scan"), 125 s ("2 min scan"), 192 s ("3 min scan"), 397 s ("6 min scan"), 780 s ("13 min scan"), 1020 s ("17 min scan"), 4560 s ("1 h scan")

Unless indicated otherwise, when calculating the peak positions from the XRPD-data, the data was first stripped from the contribution from CuKα2 and was then corrected against an internal standard (Al$_2$O$_3$).

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation. For example, persons skilled in the art of XRPD will realise that the relative intensities of peaks may vary according to the orientation of the sample under the test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractometry", John Wiley & Sons, 1996).

Dynamic Vapor Sorption (DVS)

Approximately 2-16 mg of the sample was weighed into a metal receptacle, which was then released of static electricity. The metal receptacle was positioned in a Surface Measurements System Ltd DVS Advantage instrument. The sample was subjected to two consecutive sorption-desorption cycles, each running from 0-95-0% relative humidity (% RH). One cycle consisted of 21 steps, those between 0-90% RH were taken in 10% RH each. At each stage the following equilibrium criteria was used: dm/dt over 5 minutes <0.002% and the minimum and maximum time at each stage were 10 and 360 min respectively.

The starting material 1,1-dioxo-3,3-dibutyl-5-phenyl-7-methylthio-8-(N-{(R)-1'-phenyl-1'-[N'-(t-butoxycarbonyl-methyl)carbamoyl]methyl}carbamoylmethoxy)-2,3,4,5-tetrahydro-1,5-benzothiazepine can be prepared as described in WO02/50051.

EXAMPLES

Preparation of Form a Monohydrate

Form A monohydrate can be prepared according to the methods described in PCT application number PCT/EP2014/058432, filed Apr. 25, 2014, which is referred to therein as crystal modification IV. Briefly, form A can be prepared by mixing 100 mg of any dry solid material of Elobixibat with 2 mL ethanol, in a closed vessel for a week. The solid is then isolated and dried in vacuum at elevated temperature until the ethanol has been dried off. Finally, the solid is exposed to humid air at ambient temperature until highly crystalline form A monohydrate has been formed.

Figure 8:
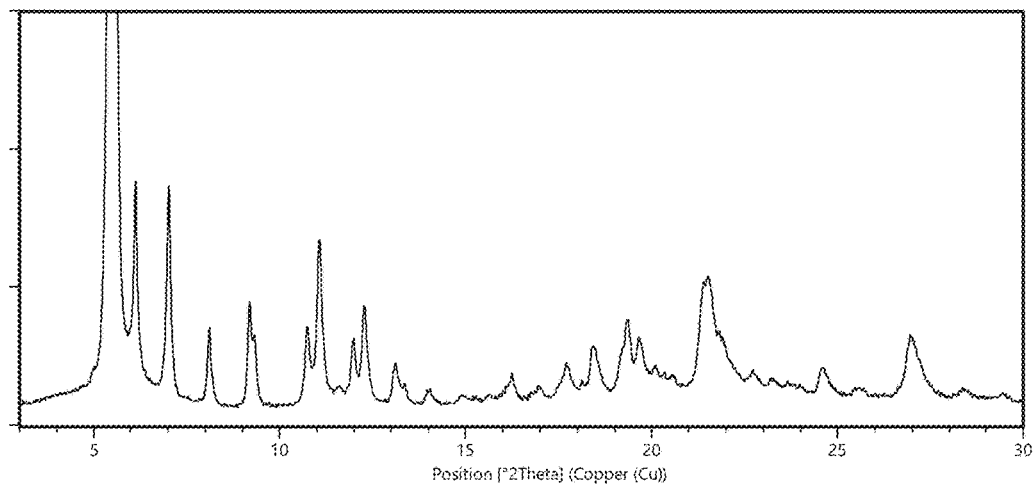
FIG. 8 shows the X-ray powder diffractogram of crystal modification G.

Preparation of Form G MIBK Solvate and Form F Anhydrate 102 mg of Elobixibat form A monohydrate was dissolved in 0.5 mL methyl isobutyl ketone (MIBK) in a 10 mL test tube at 60° C. N-heptane was then added in portions of 0.1 mL over a period of 2 hours. When 0.6 mL n-heptane had been added precipitation occurred. The vessel was then left stirred for 4 days until a thick white slurry had formed. The vessel was cooled to 21-22° C. and then a sample of the slurry was withdrawn with a Pasteur pipette and put on a cut Silicon zero background holder (ZBH). The wet sample was analyzed with XRPD, which showed that it consisted of form G MIBK solvate (FIG. 8).

A sample of the slurry was dried over night at 100° C. in vacuum and was then analyzed with XRPD. This showed that it was now form F anhydrate (FIG. 1).

Figure 9:
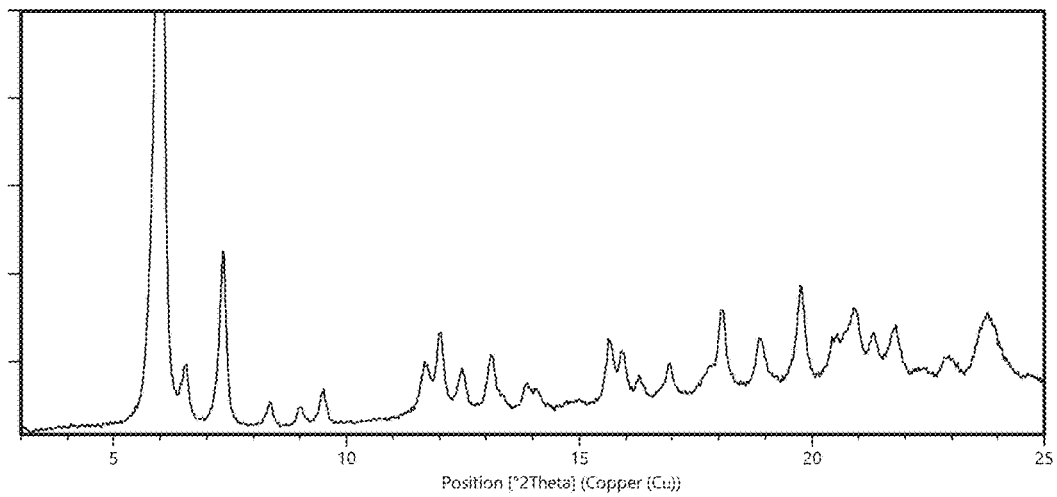
FIG. 9 shows the X-ray powder diffractogram of crystal modification H.

Preparation of Form H Ethyl Acetate Solvate and Form F Anhydrate 441 mg of Elobixibat form A monohydrate, 0.6 mL ethyl acetate and 0.6 mL n-heptane was added to a 10 mL test tube. A stirring magnet was added, the vessel was closed and was then stirred for 2 days at 62° C. The slurry was sampled to a hot (60° C.) porous Alumina XRPD substrate and analyzed with XRPD, which showed that it consisted of form H ethyl acetate solvate (FIG. 9).

A sample of the solid was dried at 100° C. in dry nitrogen gas and was then analyzed with XRPD. It consisted of form F anhydrate (FIG. 2). Alternatively, the sample was dried at 100° C. in a vacuum for 7.5 hours.

Figure 10:
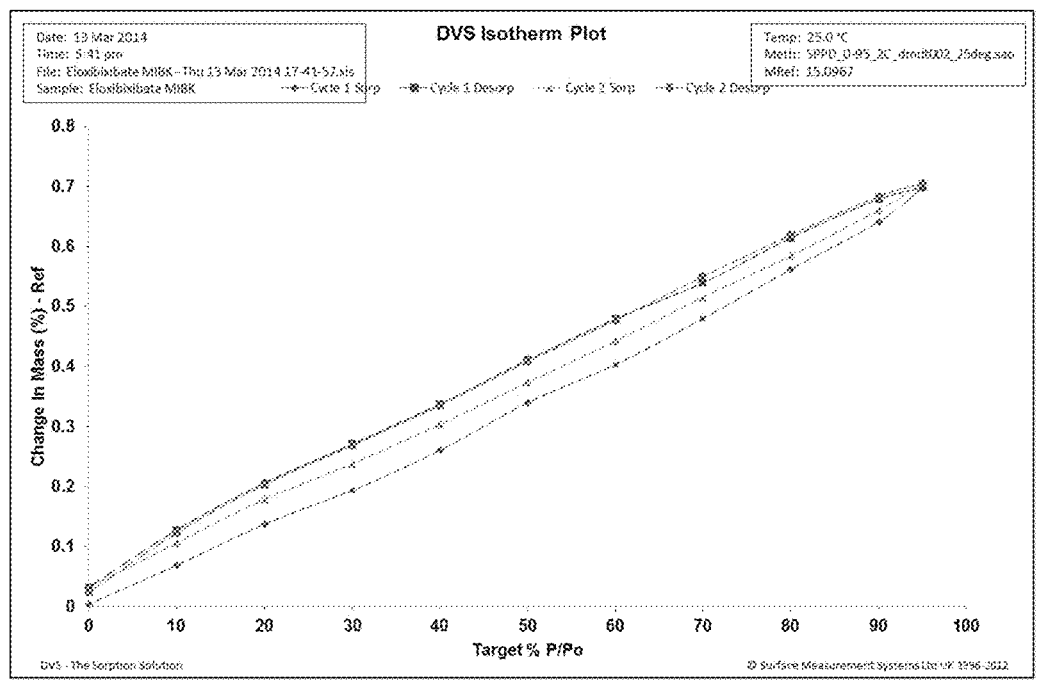
FIG. 10 shows the DVS isotherm plot of crystal modification F. The four curves show sorption and desorption for two consecutive DVS-cycles. The x-axis shows the % RH change and the y-axis shows the sample respond in weight % water.

DVS-data for crystal modification F is given in FIG. 10. As can be seen, the moisture uptake is a linear function of % RH.

Preparation of Form E Dihydrate and Form C Anhydrate 111 mg of Elobixibat form A monohydrate was weighted into a 10 mL test tube. A magnetic flea and 2.0 mL of an acetone: water 50:50% v/v mixture was added. This produced a gel-like material, which had to be hand-stirred and vigorously shaken for a couple of minutes, before the test-tube could be closed and put on magnetic stirring, at 21-22° C. Two days later a sample of the white slurry was withdrawn with a Pasteur pipette and put on a cut Silicon zero background holder (ZBH). The wet sample was analyzed with XRPD, which showed that it consisted of form E dihydrate (FIG. 7).

Approximately half of the contents of the test tube was poured into a crystallization bowl, which was then dried in vacuum for 2 hours at 60° C. This sample was then analyzed with XRPD, which showed that it consisted of form C anhydrate (FIG. 3).

Figure 11:
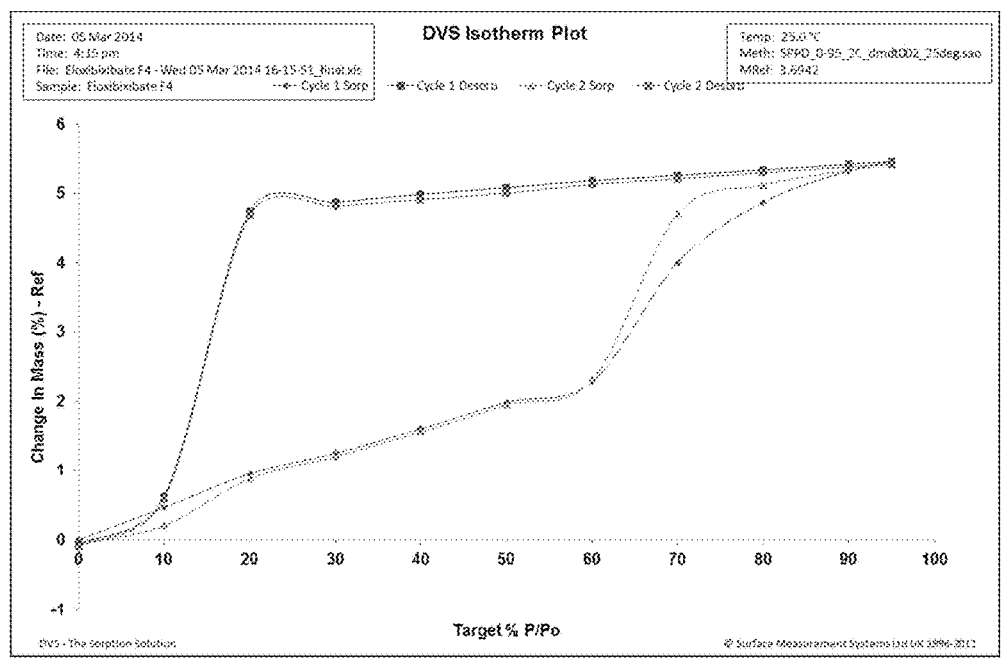
FIG. 11 shows the DVS isotherm plot of crystal modifications C and E. The four curves show sorption and desorption for two consecutive DVS-cycles. The x-axis shows the % RH change and the y-axis shows the sample respond in weight % water.

DVS-data for the transformation between crystal modifications C and E is shown in FIG. 11. The lower curves, which show a significant change in moisture between 60-70% RH, indicating the phase change from modification C to E, are the two sorption cycles. The upper curves, which show the change in moisture for the reverse phase transition between 20-10% RH, are the desorption curves. The hysterisis between the sorption and the desorption curves are due to kinetic reasons. The theoretical moisture amount for a dihydrate is 4.9% w/w fits well with the four curves coinciding around 5% w/w.

Figure 12:
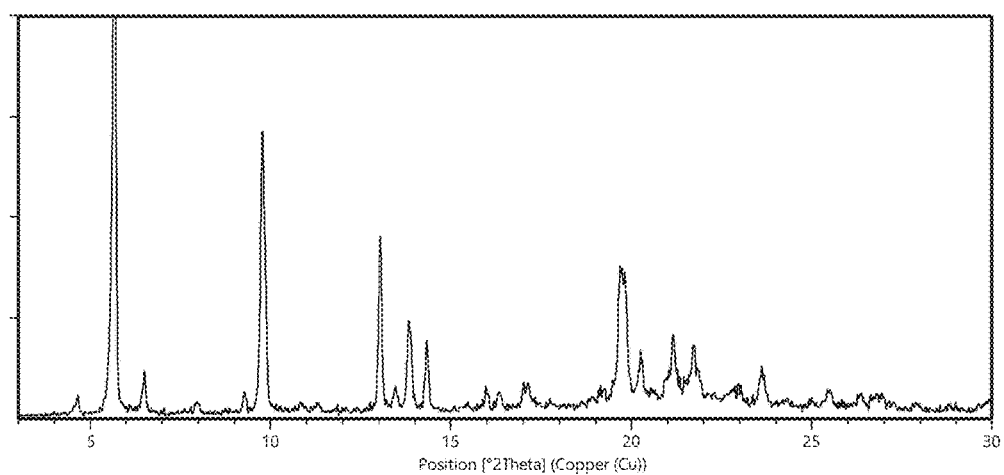
FIG. 12 shows the X-ray powder diffractogram of crystal modification D.

Preparation of Form D Solvate and Form C Anhydrate 95 mg of Elobixibat form A monohydrate was weighted into a 10 mL test tube. A magnetic flea and 2.0 mL of ethyl acetate was added. This produced a slurry, which was put on magnetic stirring, at 21-22° C. Two days later a sample of the white slurry was withdrawn with a Pasteur pipette and put on a cut Silicon zero background holder (ZBH). The wet sample was analyzed with XRPD, which showed that it consisted of form D solvate (FIG. 12). The XRPD-sample was stored for 3 days at 21-22° C. and 30% relative humidity and was then re-analyzed with XRPD. It now contained form C anhydrate (FIG. 4).

Figure 13:
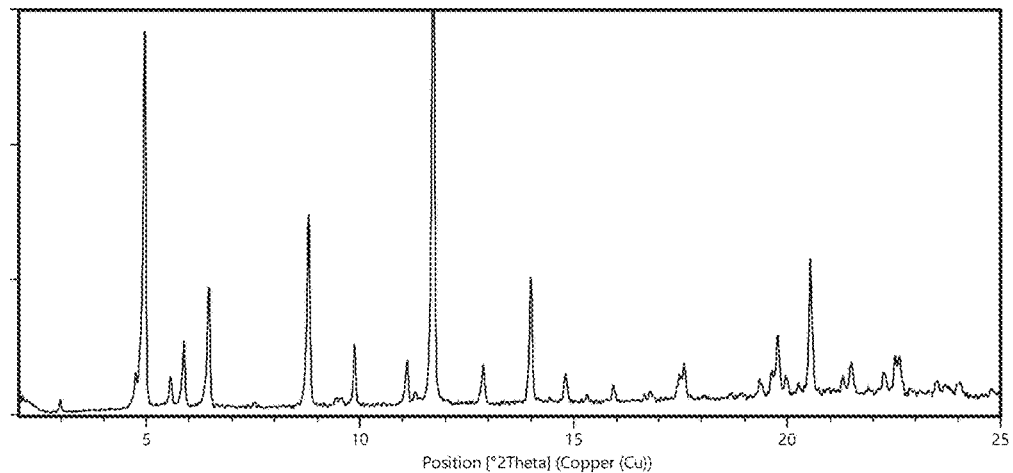
FIG. 13 shows the X-ray powder diffractogram of crystal modification M.

Preparation of Form M Acetonitrile Solvate and Form L Anhydrate 99 mg of Elobixibat form A monohydrate was weighted into a 10 mL test tube. A magnetic flea and 2.0 mL of acetonitrile was added. This dissolved the solid but it precipitated again rapidly, thus forming a slurry. The test tube was closed and put on magnetic stirring, at 21-22° C. Two days later a sample of the white slurry was withdrawn with a Pasteur pipette and put on a cut Silicon zero background holder (ZBH). The wet sample was analyzed with XRPD, which showed that it consisted of form M acetonitrile solvate (FIG. 13).

The slurry was poured into a crystallization bowl and was left to dry up in open lab air. It was then dried 6 hours in vacuum and 100° C. After cooling down in a desiccator with dry silica gel it was analyzed with XRPD. It consisted of form L anhydrate (FIG. 5).

Preparation of Form N Dihydrate

A flat sample of form L anhydrate was moistened by adding drops of water on top of it. Due to the hydrophobic properties of the solid the drops were taken up very slowly by the solid. When the water had been taken up by the sample it was analyzed with XRPD and then consisted of form N dihydrate (FIG. 6).

Figure 14:
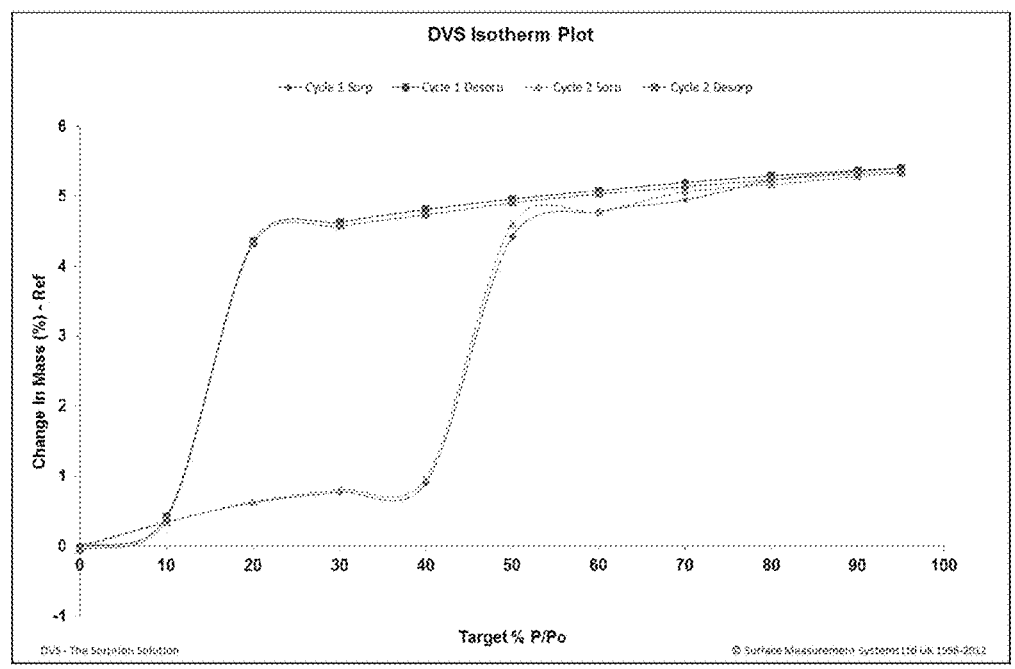
FIG. 14 shows the DVS isotherm plot of crystal modification L and N. The four curves show sorption and desorption for two consecutive DVS-cycles. The x-axis shows the % RH change and the y-axis shows the sample respond in weight % water.

DVS-data for the transformation between crystal modifications L and N is given in FIG. 14. The lower curves, which show a significant change in moisture between 40-50% RH, indicating the phase change from modification L to N, are the two sorption cycles. The upper curves, which show the change in moisture for the reverse phase transition between 20-10% RH, are the desorption curves. The hysterisis between the sorption and the desorption curves are due to kinetic reasons. The theoretical moisture amount for a dihydrate is 4.9% w/w fits well with the four curves coinciding around 5% w/w.

Preparation of Form N Dihydrate Directly from a Slurry 30 mg of elobixibat was weighted into a 1.0 mL test tube. A magnetic flea and 0.5 mL of a 2-propanol:water 50:50% v/v mixture was added. The test-tube was closed and put on magnetic stirring, at 5° C. One week later a sample of the white slurry was withdrawn with a Pasteur pipette and put on a porous Corundum sample holder. The wet sample was analyzed with XRPD, which was consistent with that of form N dihydrate.

CONCLUSIONS

Figure 15:
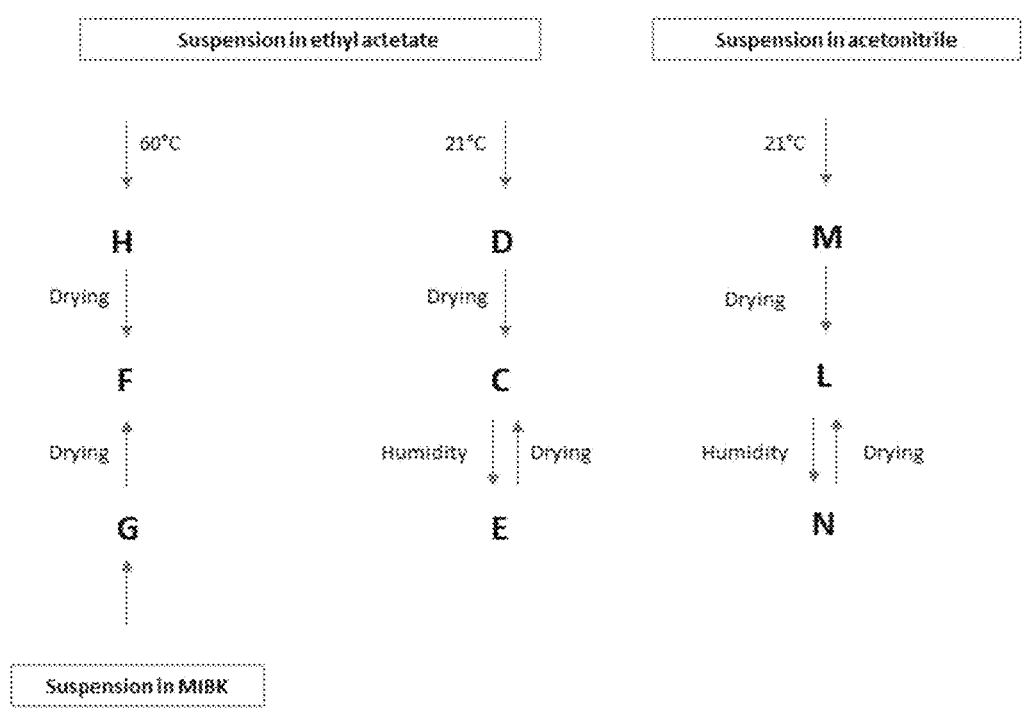
FIG. 15 shows a conversion diagram for a number of the crystal modifications described herein.

A summary of the solid state behavior of elobixibat described in this application is found in FIG. 15.

The invention claimed is:

1. A crystalline form of elobixibat, wherein the form includes void volumes that are capable of containing a substantially stoichiometric amount of water, provided that the stoichiometric amount of water is not 0.9-1.1 moles per mole of elobixibat.

2. The crystalline form of claim 1, which is a crystalline anhydrate of elobixibat, wherein the anhydrate is stable at a relative humidity of 10% at a temperature of 20° C.

3. The anhydrate of claim 2, which is crystal modification F of elobixibat, having an XRPD pattern, obtained with CuKα1-radiation, with peaks at °2θ positions 6.1±0.2 and 5.9±0.2 and with peaks at one or more °2θ positions of: 6.6±0.2, 8.3±0.2, and 11.9±0.2.

4. The anhydrate of claim 2, which is crystal modification C of elobixibat, having an XRPD pattern, obtained with CuKα1-radiation, with peaks at °2θ positions 12.4±0.2 and 5.8±0.2 and with peaks at one or more °2θ positions of: 4.8±0.2, 8.2±0.2, 9.9±0.2, 10.9±0.2, 16.6±0.2, 19.8±0.2 and 20.6±0.2.

5. The anhydrate of claim 2, which is crystal modification L of elobixibat, having an XRPD pattern, obtained with CuKα1-radiation, with peaks at °2θ positions 6.4±0.2 and 12.7±0.2 and with peaks at one or more °2θ positions of: 4.2±0.2, 8.5±0.2, 10.5±0.2, 19.3±0.2 and 19.5±0.2.

6. The crystalline form of claim 1, which is a crystalline dihydrate of elobixibat, wherein the dihydrate is stable in contact with water.

7. The dihydrate of claim 6, wherein the dihydrate can be crystallized directly from a slurry.

8. The dihydrate of claim 6, which is crystal modification N of elobixibat, having an XRPD pattern, obtained with CuKα1-radiation, with the most significant peaks at °2θ positions 6.1±0.2, 8.0±0.2 and 12.0±0.2.

9. The dihydrate of claim 6, which is crystal modification E of elobixibat, having an XRPD pattern, obtained with CuKα1-radiation, with the most significant peaks at °2θ positions 6.1±0.2, 12.1±0.2 and 20.9±0.2.

10. A solid pharmaceutical composition comprising the crystalline form of claim 1 and a pharmaceutically acceptable diluent or carrier.

11. The solid pharmaceutical composition according to claim 10, wherein the chemically purity of the crystalline form is >99%.

12. A method for the treatment of a disease selected from the group consisting of constipation, chronic constipation, functional constipation, and constipation predominant irritable bowel syndrome (IBS-C) in a subject in need thereof, the method comprising administering to the subject a therapeutically effective amount of the crystalline form of claim 1.

13. A method for the treatment of non-alcoholic fatty liver disease (NAFLD), the method comprising administering to the subject a therapeutically effective amount of the crystalline form of claim 1.

14. A method for the treatment of non-alcoholic steatohepatitis (NASH), the method comprising administering to the subject a therapeutically effective amount of the crystalline form of claim 1.

15. A solid pharmaceutical composition comprising the crystalline anhydrate of claim 2 and a pharmaceutically acceptable diluent or carrier.

16. The solid pharmaceutical composition according to claim 15, wherein the chemically purity of the crystalline anhydrate is >99%.

17. A method for the treatment of a disease selected from the group consisting of constipation, chronic constipation, functional constipation, and constipation predominant irritable bowel syndrome (IBS-C) in a subject in need thereof, the method comprising administering to the subject a therapeutically effective amount of the crystalline anhydrate of claim 2.

18. A method for the treatment of non-alcoholic fatty liver disease (NAFLD), the method comprising administering to the subject a therapeutically effective amount of the crystalline anhydrate of claim 2.

19. A method for the treatment of non-alcoholic steatohepatitis (NASH), the method comprising administering to the subject a therapeutically effective amount of the crystalline anhydrate of claim 2.

20. A solid pharmaceutical composition comprising the crystalline dihydrate of claim 6 and a pharmaceutically acceptable diluent or carrier.

21. The solid pharmaceutical composition according to claim 20, wherein the chemically purity of the crystalline dihydrate is >99%.

22. A method for the treatment of a disease selected from the group consisting of constipation, chronic constipation, functional constipation, and constipation predominant irritable bowel syndrome (IBS-C) in a subject in need thereof, the method comprising administering to the subject a therapeutically effective amount of the crystalline dihydrate of claim 6.

23. A method for the treatment of non-alcoholic fatty liver disease (NAFLD), the method comprising administering to the subject a therapeutically effective amount of the crystalline dihydrate of claim 6.

24. A method for the treatment of non-alcoholic steatohepatitis (NASH), the method comprising administering to the subject a therapeutically effective amount of the crystalline dihydrate of claim 6.

\* \* \* \* \*